United States Patent [19]

Kammerer et al.

[11] Patent Number: 4,690,842
[45] Date of Patent: Sep. 1, 1987

[54] REINFORCED CASTING MATERIAL

[75] Inventors: Gene W. Kammerer, East Brunswick; Hee K. Yoon, North Brunswick; Robert Li-Jiun Sun, Stanhope, all of N.J.

[73] Assignee: Johnson & Johnson Products, Inc., New Brunswick, N.J.

[21] Appl. No.: 5,492

[22] Filed: Jan. 20, 1987

Related U.S. Application Data

[63] Continuation-in-part of Ser. No. 784,297, Oct. 7, 1985, Pat. No. 4,643,909.

[51] Int. Cl.⁴ ............... A61L 15/00; A61F 13/00
[52] U.S. Cl. .................................. 428/35; 128/90; 206/524.1; 427/2; 427/407.1; 428/423.3; 428/703
[58] Field of Search ............ 128/90; 206/524.1; 427/2, 407.1; 428/35, 423.3, 703, 425.6

[56] References Cited

U.S. PATENT DOCUMENTS

| | | | |
|---|---|---|---|
| 3,387,833 | 6/1968 | Whittaker et al. | 432/59 |
| 4,411,262 | 10/1983 | Von Bonin et al. | 428/425.6 |
| 4,423,829 | 1/1984 | Katz | 222/95 |
| 4,427,003 | 1/1984 | Fennimore et al. | 428/425.6 |
| 4,433,680 | 2/1984 | Yoon | 128/90 |
| 4,498,467 | 2/1985 | Kirkpatrick et al. | 128/90 |
| 4,502,479 | 3/1985 | Garwood et al. | 128/90 |
| 4,511,626 | 4/1985 | Schumacher | 428/425.6 |
| 4,539,345 | 9/1985 | Hansen | 428/425.6 |

Primary Examiner—William J. Van Balen
Attorney, Agent, or Firm—Michael Q. Tatlow

[57] ABSTRACT

A composition with reduced tack used to reinforce polyurethane casts is disclosed. The composition has controlled foaming activity and a viscosity between 100,000 and 1,000,000. The foaming activity and viscosity and reduced tack allow the formulation to be readily applied to the cast area that is to be reinforced.

13 Claims, 4 Drawing Figures

REINFORCED CASTING MATERIAL

This application is a continuation-in-part of application Ser. No. 784,297 filed Oct. 7, 1985 now U.S. Pat. No. 4,643,909.

The present invention relates to a composition which can be employed to reinforce casts which have been made from polyurethane casting tapes and to a method of applying such reinforcing material to casts made from polyurethane casting tapes.

BACKGROUND OF THE INVENTION

Plaster of Paris casts have been used to immobilize body members for some time. These bandages are made by depositing plaster of Paris on reinforcing scrim material such as gauze. The plaster of Paris is activated by dipping the cast bandage in water and then applying the bandage to a patient. In recent years, new casting materials have replaced plaster of Paris as the hardening agent in the cast bandage. This new material is a water hardenable polyurethane. After curing the polyurethane offers advantages over plaster of Paris in that it allows transmission of x-rays through the finished casts and it is not sensitive to water as is plaster of Paris and it is also considerably lighter for a given strength in plaster of Paris.

With the use of plaster of Paris bandages, it is common to provide for reinforcement of selected areas of the cast by applying additional bandage material to a particular section of the cast which was desired to be reinforced. For example, if the cast was a walking cast, it was quite common to put a reinforcing layer of plaster of Paris around the sole of the foot of the cast and to incorporate a plug of some type so that the patient could place the cast onto the ground when walking with crutches without fear of the cast breaking. With the advent of the polyurethane casting materials, reinforcement has been performed in substantially the same manner; that is additional strips of the polyurethane impregnated substrates have been applied to the cast where reinforcement is desired. The application of additional strips or segments of polyurethane casting tape is somewhat difficult because of the nature of the polyurethane polymer which is the hardening material in these tapes. The polyurethane becomes tacky during the curing cycle before it begins to harden. It is difficult for one person to cut a piece of polyurethane casting tape, wet the cut tape and then apply the cut section to the cast to obtain the reinforcement and smooth the reinforcement section into the cast while the tape is tacky. The polyurethane casting tapes harden rapidly and lose their tackiness and it is difficult to finish the reinforcement before the tape cures and hardens.

SUMMARY OF THE PRESENT INVENTION

Applicants have discovered that it is possible to reinforce polyurethane casts by the application of a curable liquid resin to the casting tapes as the casting tapes are applied to the patient. Although many curable resin systems, such as unsaturated polyesters or epoxies, will function for this purpose, the preferred resin system is a polyurethane prepolymer formulation similar to the prepolymer employed in the manufacture of the casting tape. The use of a polyurethane prepolymer formulation assures compatability of the reinforcement with the polyurethane of the casting tape and allows the use of water as the curing agent. The polyurethane prepolymer formulation employed as the reinforcing material is preferably a foaming polyurethane formulation of a viscosity such that the polyurethane prepolymer can be readily distributed over the areas of the cast where reinforcement is desired. The reinforcing prepolymer differs from the prepolymer that is used in the tape in that the reinforcing prepolymer has a controlled degree of foaming. The polyurethane prepolymer used to impregnate casting tape contains a small amount of an antifoam agent to prevent the prepolymer from foaming, and because of the relatively small amount of prepolymer coated on the tape substrate, foaming is not a problem in casting tapes. The viscosity of the reinforcing polyurethane prepolymer is also more important in the present invention as compared to the viscosity of the prepolymer that is used to impregnate substrates to form the casting tape. The reinforcing polyurethane prepolymer contains a tack reducing agent such as mineral oil and/or water soluble polymers such as polyethylene oxide and polyvinylpyrrolidone. The addition of the tack reducing agent allows greater ease of application of the reinforcing prepolymer to the cast.

DETAILED DESCRIPTION OF THE INVENTION

Figure 1:
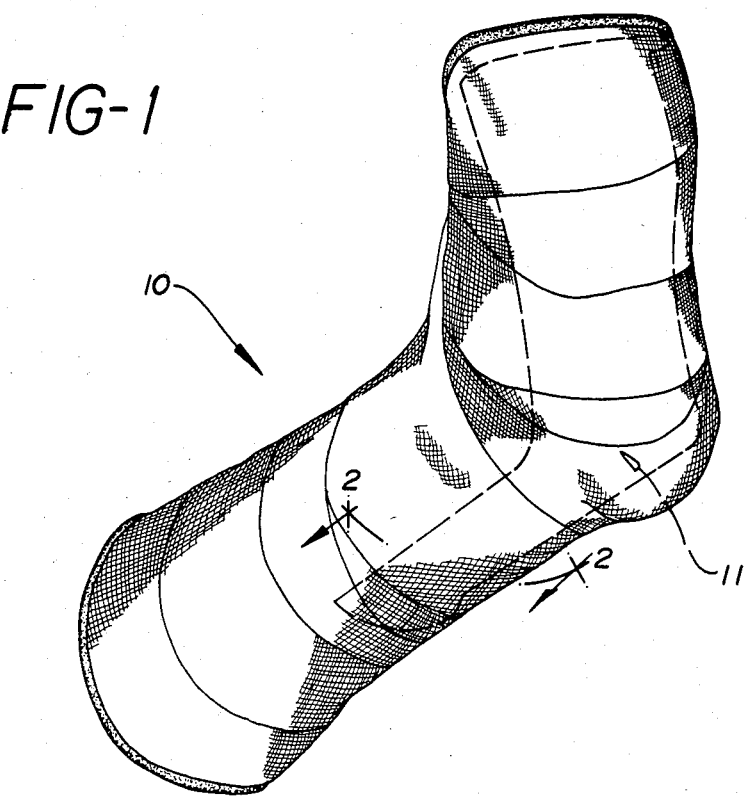
FIG. 1 is an isometric view of a leg cast showing the reinforcement area as a dotted line.

The polyurethane prepolymer of the present invention is similar in its chemistry to the prepolymers used in the polyurethane casting tapes but differs in its physical characteristics. The viscosity and foaming properties of the reinforcing prepolymer must be carefully controlled as the prepolymer is applied to the cast as a liquid and must have the proper viscosity and foaming characteristics to remain on the casting tape where applied and to be easily spreadable over that portion of the casting tape where reinforcement is desired.

The reinforcing prepolymer of the present invention may be prepared from the following isocyanates and polyols.

Isocyanates

The aromatic isocyanates useful in the prepolymer system of the present invention may be any of the aromatic polyisocyanates known in polyurethane chemistry which are described, for example, in "Polyurethanes, Chemistry and Technology," Part I, Interscience Publishers (1962). The aromatic polydisocyanates preferred include toluene diisocyanate (TDI), such as the 80/20 or the 65/30 isomer mixture of the 2,4 and 2,6 isomeric forms; diphenylmethane, diisocyanate (MDI), such as the 4,4', the 2,4' and the 2,2' isomeric forms or isomeric mixtures thereof; modified MDI containing additional functional groups such as carbodiimide groups, urethane groups, and allophanate groups and polymethylene (poly)phenyldiisocyanates (Polymeric MDI) which are derived from phosgenation of the condensation products of aniline and formaldehyde. The most preferred isocyanate is the carbodiimide containing MDI which is readily available commercially, e.g., Isonate® 143L and Rubinate® XI-168.

Polyols

The polyols useful in the prepolymer system of the present invention include polyether polyols and polyester polyols. The polyether polyols may be prepared by the polymerization of epoxides, such as ethylene oxide, propylene oxide, butylene oxide, tetrahydrofuran, styrene oxide, or mixtures thereof in the presence of catalysts.

The polyester polyols include the reaction products of polyhydric alcohols and polybasic carboxylic acids. Instead of free carboxylic acids, the corresponding polycarboxylic acid anhydrides or the corresponding polycarboxylic acid esters of low alcohols or mixtures thereof may be used for preparing the polyesters. Polyesters of lactones, such as ε-caprolactone may also be used.

Most preferred polyols are the poly(oxypropylene) diols and triols, having a molecular weight of from 400 to 2,000. Examples of such polyols are Pluracol® P-1010 available from BASF Wyandotte Corp. and Poly G® 36-232 available from Olin Corp.

The preferred polyurethane prepolymer is made from diphenylmethanediisocyanate containing carbodiimide groups. These diisocyanates are reacted with a polyol containing two to three functional groups. The polyols may be diols or triols or mixtures of diols and triols. The preferred polyols are poly(oxypropylene)glycol having a hydroxyl number of 105 and poly(oxypropylene) triol having a hydroxyl number of 232. The molecular weight of the polyols is preferably in the range of 700 to 1,500, and most preferably between 700 and 1,100.

The ratio of the polyisocyanate to the polyol in the prepolymer reaction mixture is best expressed by the equivalent ratio. Equivalent weight is determined by dividing the molecular weight of each particular component by its functionality or number of functional groups in the compound. The equivalent ratio is the ratio of the equivalency of the isocyanate to the polyol. The equivalent ratio in the present system should be between 2:1 to approximately 15:1 equivalents of the polyisocyanate to the polyol and preferably from 2:1 to 10:1. These components are combined so that there is an excess of from 5% to 30% NCO groups in the prepolymer. The prepolymer also contains from 0.1% to 10% by weight, based on the weight of the total mixture, of dimorpholinodiethylether, available as Thancat DMDEE from Texaco, Inc., as a catalyst. Other suitable catalysts may also be employed.

In addition to the isocyanates and polyols, the formulation of the present invention contains a catalyst, as indicated above and a stabilizer, such as benzoyl chloride and a combination of a thickening agent and an antifoam agent in sufficient amounts to control the viscosity and the foaming of the formulation when the formulation is applied to a cast on a patient.

The antifoam or defoamer in the formulation should be inert, i.e., not reactive with the other ingredients in the formulation. Typical antifoam agents used in polyurethane formulations are polydimethylsiloxane, phenylmethylsiloxane and hydrophobic silica in high molecular weight hydrocarbon oils.

The antifoam agent in the formulation is preferably polydimethylsiloxane having a viscosity of 30,000 centistokes. It is commonly used as an antifoam agent for polyurethanes. The formulation of the present invention contains from 0.07 to 7.5% by weight, based on the total weight of the formulation, of the antifoam agent. The preferred amount of the antifoam agent is from about 3% to 5% by weight. In the usual polyurethane prepolymer employed to coat the substrates in casting tapes, the antifoam agent is present in an amount of from about 0.01% to 1% by weight. The additional antifoam agent is necessary in the reinforcing prepolymer formulation because the formulation is applied in relatively large amounts as compared to the prepolymer coating on a casting tape substrate. If the formulation foams excessively, it will be too difficult to properly apply to the cast on the patient and will tend to become too fluid and drip off the cast.

In addition to the antifoam agent, the present formulation also contains a thickening agent. The thickening agent assists in controlling the viscosity of the prepolymer so that it may be applied to the cast and easily spread over the area to be reinforced. The thickening agent must also be inert and not reactive with the other ingredients in the formulation. Typical thickening agents that can be used include cosmetic grade talc; fumed silica; organic polymer powders such as polymethylmethacrylate; aryl ureas such as naphthyl urea and indanthrene. The preferred thickening agent is a fumed silica sold as Aerosil R974 by Degussa Inc. The thickening agent and the antifoam control the viscosity of the formulation. The viscosity may be between 100,000 and 1,000,000 centipoise (CPS) measured with a Model RVF Brookfield viscometer with a number 7 spindle at 4 RPM and 24° C. by ASTM D1638. The preferred viscosity is between 300,000 and 800,000. The thickener should be present in an amount of from 2 to 6% by weight based on the total weight of the formulation to give the desired viscosity.

It is the combination of the thickening agent and the antifoam agent that controls the viscosity of the formulation. Increasing the level of one of the agents while decreasing the level of the other will not necessarily result in the proper viscosity. Applicant has found that the combination of the indicated amounts of antifoam agent and the thickening agent will function to control the viscosity of the formulation.

The present formulation contains a tack reducing agent to reduce the tackiness and stickiness of the prepolymer formulation. The reduced tack of the formulation allows the formulation to be easily distributed or spread over the area of the cast where reinforcement is desired as the formulation will not stick to the gloved hands of the person applying the formulation to the cast.

The tack reducing agents employed in the formulation are mineral oil or the water soluble polymers such as those disclosed in our copending application, Ser. No. 913,809, filed Sept. 30, 1986. These water soluble polymers contain repeating units of the structure $(-O-CH_2CH_2)_n$, in which n is at least 1100 and may be as high as 100,000. The weight average molecular weight (Mw) of the water soluble polymer is between 50,000 and 4,000,000. These water soluble polymers may be homopolymers of ethylene oxide or block or graft copolymers containing large lengths of the repeating units of the structure $(-O-CH_2CH_2)$ joined by bridge molecule which may be an ester, urethane or siloxane linkage. The water soluble polymer is incorporated into the polyurethane prepolymer after the prepolymer is formed. The preferred water soluble polymer is a poly(ethylene oxide) polymer that is a commercially available solid material provided by the Union Carbide Corporation under the trade name "PO-LYOX" and having a weight average molecular weight from approximately 100,000 to 4,000,000. The use of the water soluble polymers having molecular weights above 3,000,000 have a tendency to develop stringiness between the prepolymer formulation and the gloved hands of the cast technician when the formulation is applied, and are not as esthetically desirable as formulations made with a water soluble polymer having a molecular weight of 3,000,000 or less. Water soluble polyvinylpyrrolidone may also be employed. The polyvinylpyrrolidones useful in the present invention have a viscosity average molecular weight (Mv) of from 100,000 to 1,000,000. The water soluble polymer is added to the prepolymer formulation in an amount to 0.5% to 3% based on the total weight of the prepolymer formulation. The water soluble polymer is not soluble in the polyurethane prepolymer, but remains inert in the prepolymer until the formulation is contacted by water. As the water soluble polymers are very soluble in water, they dissolve rapidly and provide a slipperiness or antitack properties to the formulation when the formulation is applied to a cast.

Combinations of mineral oil in an amount of from 0.5% to 2% by weight, and the water soluble polymer in an amount of from 0.5% to 3% based on the total weight of the formulation are preferred.

Generally, the formulation of the present invention is prepared by thoroughly mixing the isocyanate, the benzoyl chloride stabilizer and the antifoam agent. To this mixture is added the polyol and the catalyst. The reaction is allowed to continue for approximately one hour after the temperature of the reactants reaches 50° C. The resultant reaction product is transferred to a planetary mixer under a nitrogen blanket and the thickening agent is added while blending the mixture to obtain a homogenous mixture of the ingredients. The tack reducing agents are then added and the mixture is blended for about 30 minutes at room temperature. The resulting formulation can be packaged or stored in a moisture-free atmosphere, such as dry nitrogen, until packaged.

After the formulation is prepared, it is packaged in a moisture-resistant container as moisture will activate the formulation. The container can be any type of container which is moisture-impervious and which lends itself to the application of the formulation to a cast. The container should have a capacity of from 2 to 16 ounces. A two ounce container will provide sufficient prepolymer to reinforce a short leg cast or a short arm cast. Larger containers, i.e., 8 to 16 ounces can be economically used in facilities where large numbers of casts are applied to patients. Examples of such containers are foil packages, tubes similar to toothpaste tubes, and pressure containers such as those disclosed in U.S. Pat. Nos. 3,387,833 and 4,423,829. When using pressure containers, a large amount of the prepolymer formulation can be filled into the container, as the container will not allow moisture to enter the container.

The formulation should foam rapidly with the foaming beginning about 30 to 40 seconds after contact with the moisture on the cast and being substantially complete about 4 minutes after contact. The amount of foaming activity can be quantified by the ratio of the final foam height to the thickness of the formulation applied. This foam rise ratio is between 4 to 1 and 16 to 1. For example, if the formulation is spread to a thickness of 1/16 of one inch, it will rise to a height of from ¼ of one inch to one inch within four minutes. This degree of foaming activity will insure that the formulation can be forced into the casting tapes previously applied to the patient, and the formulation will flow into the subsequent layer of casting tapes applied to the patient. The foam rise ratio is determined by the following procedure: A 1 foot piece of plastic backed cloth is secured on a bench with the cloth facing up. 30 ml of $H_2O$ is spread on an area of about $6'' \times 6''$. 8 grams of the resin is spread on the wetted cloth to an area of about 4" to 4". The thickness of the resin is controlled to 1/32"–1/16" by smoothing with a spatula. The resin is allowed to foam and harden. A section of the foam is then cut out, usually about 1" square, where the resin is foamed the highest, and is measured for height.

In applying the prepolymer reinforcing material to a cast, the casting tape is applied to the patient in a normal manner. Multiple layers of the casting tape are usually applied to form the cast. The present formulation is applied at a rate of between ½ to 1 gram per square inch of cast surface to be reinforced. The prepolymer reinforcing formulation can be applied at any stage in the formation of the cast after the first layer of casting tape is applied to the patient. The formulation can be applied between different wraps of casting tape or it may be applied after all of the casting tape has been applied to the patient to form the cast. The prepolymer formulation is preferably applied when the cast is still moist with water from the dipping or activation process of the casting tape. This provides the moisture necessary to cure the prepolymer reinforcing formulation. It is also possible to patch or reinforce a fully formed and cured cast by first applying water to the cast in the area where patching or reinforcement is needed and then applying the reinforcing prepolymer formulation to the area which is wet with water. The prepolymer formulation is considerably simpler to apply than a fabric strip and provides significant reinforcement to the cast.

A reinforced short leg cast is shown in FIG. 1. The cast 10 is formed in the usual manner by applying a moistened casting tape in an overlapping manner on the limb. The reinforcement area is shown by the dash lines 11 in FIG. 1. The reinforcement prepolymer is shown by the dotted area 12 in FIG. 2. It is placed between adjacent layers 13 and 14 of casting tape as hereinafter described.

Figure 2:
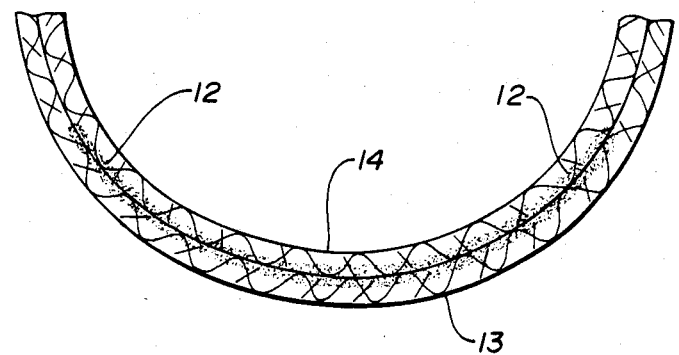
FIG. 2 is a cross-sectional view of a portion of the cast of FIG. 1, taken in the direction of the arrows in FIG. 1.
Figure 3:
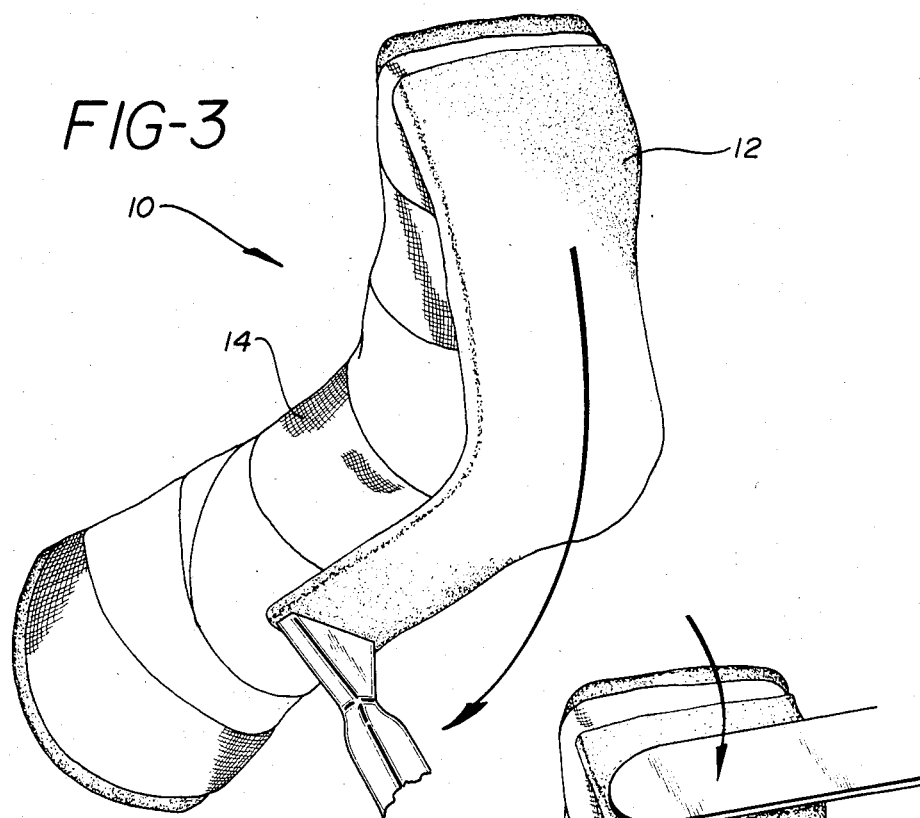
FIG. 3 is an isometric view showing the application of the prepolymer reinforcement to the cast.
Figure 4:
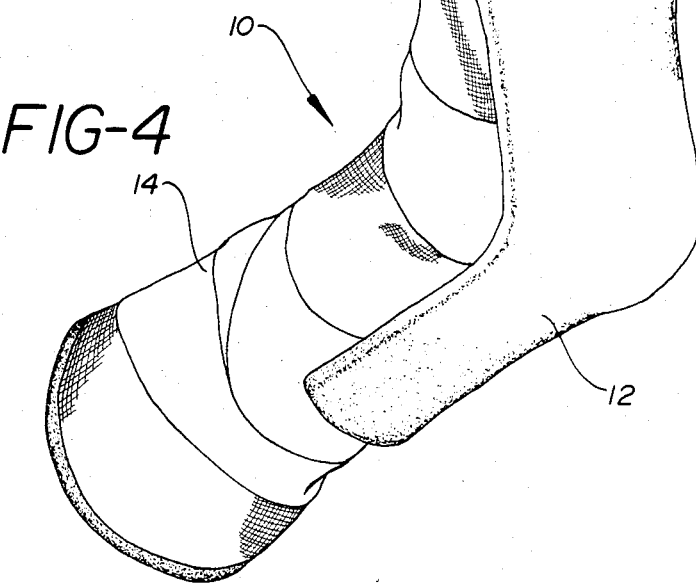
FIG. 4 is an isometric view showing the prepolymer applied in FIG. 3 being distributed over the cast.

The application of the reinforcing prepolymer to the cast is illustrated in FIGS. 3 and 4. The prepolymer is applied from a container to the portion of the cast that is to be reinforced. The prepolymer will begin to foam within about 30 seconds after it contacts the moisture on the previously applied casting tape. The prepolymer can be spread over the portion of the cast to be reinforced with a spatula, a tongue depressor or any similar tool. Spreading the prepolymer forces some of the prepolymer into the openings of the casting tape previously applied to the patient. After the reinforcing prepolymer is spread over the area of the cast to be reinforced, additional layers of casting tape are usually applied to the patient. As a layer of casting tape is applied over the area of the cast covered by the reinforcing prepolymer, the prepolymer is forced into the openings in the subsequently applied casting tape. This is illustrated in FIG. 2. The dotted area in the figure represents the reinforcing prepolymer as it extends in the openings in adjacent layers or wraps of the casting tape.

The following examples show the reinforcement of casts by using the material of the present invention. In the Examples, the Impact Test is performed in the following manner: The test cylinders are prepared and aged at a temperature between 70° and 80° F. for three days to insure the cylinders are completely cured. Each cylinder is secured onto a metal plate which supports the cylinder only on the bottom of the cylinder. A five pound projectile is dropped one foot onto the top of the cylinder. The cylinder is then inspected for damage.

EXAMPLE 1

On an artificial leg, a cast was applied using two polyurethane-fiberglass orthopedic casting tape rolls, four inches wide and four yards long. After the application of the first tape, three layers of the tape covered the heel and the foot area. Thirty grams of the reinforcing polyurethane prepolymer of the present invention was applied in a strip approximately two inches wide starting at the ball of the foot to the heel and upward a distance of approximately 4 inches from the back of the heel. A second casting tape bandage was then applied over the first to build a total of six layers of casting tape. Fifteen minutes after the application of the final tape, the heel section of the cast was cut out and tested on a Chatillon Compression Tester in which the top platen had been replaced by a one inch diameter ball. The samples were compressed a distance of approximately one centimeter. In the first test, 165 pounds of resistance was required to compress the cast section one centimeter. The test was repeated ten times with no loss in the strength necessary to compress the cast section the distance of one centimeter.

The formulation of the prepolymer used in this Example was as follows:

|  | Weight % |
|---|---|
| Isonate 143L (NCO content 29.0%) | 62.96 |
| Pluracol P-1010 | 19.49 |
| Poly-G-36-232 | 12.81 |
| Thancat DMDEE | 1.67 |
| Benzoylchloride | 0.05 |
| Dow Corning 200 Fluid 30,000 cs | 0.07 |
| Aerosil R-974 (SiO$_2$) | 2.95 |

EXAMPLE 2

The procedure of Example 1 was repeated using approximately twenty-six grams of the same prepolymer of the present invention. The test showed that it required 170 pounds resistance on the first test and no loss of strength after the test had been repeated ten times.

EXAMPLE 3

A third cast was made using the same technique as in Example 1 except there was no reinforcing polymer added to the cast. Under the same test conditions as in Example 1, this sample showed 195 pounds of resistance on the first compression, but only 85 pounds after the tenth compression, indicating the superior strength of the reinforced casts of Examples 1 and 2.

EXAMPLE 4

Cylinders of cast material were prepared by forming a test cylinder around a dowel which was approximately two and three-quarter inches in diameter. The test cylinders were multiple wraps of four inch wide casting tape. Test cylinders were made with four or five layers of a standard polyurethane-fiberglass casting tape. In some of the test cylinders, six grams of the polyurethane reinforcing resin were applied as a two inch wide strip along the length of the four inch cylinder. A five pound projectile was dropped from a height of one foot onto the top of the cylinders on the area where the reinforcing resin was applied and the integrity of the cylinders was determined by observing cracks and delamination of the various layers of the fiberglass material. Three cylinders were made for each test and the number of drops of the projectile to failure were noted. The results are reported in the table below. Cylinders A were made from four layers of fiberglass casting tape with no reinforcing resin. Cylinders B were made with four layers of fiberglass tape and six grams of the liquid reinforcing resin was applied between the second and third layer of the fiberglass tape as the tape was wrapped. Cylinders C were made from five layers of fiberglass casting tape with no reinforcing resin. Cylinders D were made with five layers of fiberglass casting tape, and six grams of the prepolymer reinforcing material was applied between the third and fourth layer of the casting tape. The results of the test are shown in Table 4.

In Table 4 the data shows that in the samples where the polyurethane reinforcing resin was applied there was no visible damage. However, in the unprotected areas, cracks and delamination occurred, indicating that selective areas of a cast may be protected by the application of the reinforcing resin.

TABLE 4

| Sample | No. of impacts | Condition of cylinders Cracking of Top | Sides | Side delamination |
|---|---|---|---|---|
| A | 3 | Yes | Yes | Yes |
| B | 3 | No | Yes | No |
| C | 10 | Yes | Yes | Yes |
| D | 10 | No | Yes | No |

The formulation for the polyurethane prepolymer used in Example 4 was as follows:

|  | Weight % |
|---|---|
| Isonate 143L (NCO content 29.0%) | 60.11 |
| Pluracol P-1010 | 18.02 |
| Poly-G-36-232 | 12.32 |
| Thancat DMDEE | 1.60 |
| Benzoylchloride | 0.05 |
| Dow Corning 200 Fluid 30,000 cs | 5.00 |
| Aerosil R-974 (SiO$_2$) | 2.87 |

EXAMPLE 5

The impact testing conditions of Example 4 were repeated except that the prepolymer reinforcing splint was applied to the cylinders in a one to one and one-half inch wide strip around the cylinder in an amount of from 8 to 9 grams per cylinder. The prepolymer was the same as that used in Example 4. The results are reported in the following table.

Cylinders A were made with four layers of casting tape and no reinforcing resin. Cylinders B were made with four layers of a fiberglass tape with the liquid reinforcing material applied between the second and third layer. Cylinders C were made with five layers of fiberglass tape with no reinforcing material. Cylinders D were made with five layers of fiberglass tape with the reinforcing material applied between the third and fourth layer.

TABLE 5

| | Cylinder # | | |
|---|---|---|---|
| | 1 | 2 | 3 |
| | | Hits to Failure | |
| A | 2 | 2 | 3 |
| | | Cracked on top and sides delaminated. | |
| B | 10 | 13 | 13 |
| | | Cracked on top from the reinforced area to the edge of the cylinder. | |
| C | 19 | 16 | 18 |
| | | Cracked and delaminated on sides and top. | |
| D | 50 | 75 | 80 |
| | | Cracked and delaminated from reinforced area to the edge of the cylinder. | |

The test results show the overall increased strength which can be imparted to a cast by applying the reinforcing resin around a larger area of the cast, i.e., the entire circumference of the cast.

EXAMPLE 6

A reinforcing prepolymer formulation was prepared having the following composition:

| | Weight percent |
|---|---|
| Isonate 143 L | 59.46 |
| Pluracol P-1010 | 18.40 |
| Poly-G-36-232 | 12.10 |
| Thancat DMDEE | 1.58 |
| Benzoylchloride | 0.05 |
| Dow Corning 200 Fluid | 4.89 |
| Aerosil R-974 | 3.52 |

The viscosity of the formulation was 180,000.

Two four inch-wide cast cylinders were prepared using five layers of a polyurethane casting tape. The reinforcing prepolymer was applied to the cylinders between the third and fourth layers of tape. The reinforcing prepolymer was applied as a band 1½ inches wide around the entire cylinder. The prepolymer began to foam 0.5 minutes after application and foaming was complete after 2.1 minutes. The density of the foam was 0.08 g/ml. The completed cylinders weighed 69.5 grams. The cylinders were impact tested three days after the cylinders were formed. The cylinders were subjected to 100 impacts with a five pound projectile with no cracking or other failure.

EXAMPLE 7

A reinforcing prepolymer formulation was prepared having the following composition:

| | Weight percent |
|---|---|
| Isonate 143 L | 58.08 |
| Pluracol P-1010 | 17.98 |
| Poly-G-36-232 | 11.82 |
| Thancat DMDEE | 1.55 |
| Benzoylchloride | 0.55 |
| Dow Corning 200 Fluid | 4.78 |
| Aerosil R-974 | 4.61 |

The viscosity of the formulation was 480,000 cps.

Two 4 inch-wide test cylinders were prepared using five layers of a polyurethane casting tape. The reinforcing prepolymer was applied between the third and fourth layer of casting tape. The reinforcing prepolymer was applied as a band 1½ inches wide around the entire cylinder. The prepolymer began to foam 0.2 minutes after application and foaming was completed in 1½ minutes. The density of the foam was 0.1 gm/ml. The cylinders weighed 69.5 grams. The cylinders were impact tested three days after the cylinders were formed. The cylinders were subjected to 100 impacts on the reinforced area with a five pound projectile with no cracking or other failure.

EXAMPLE 8

A polyurethane prepolymer was prepared by charging 6407 parts of ISONATE 143L, 7.30 parts of Dow Corning 200 fluid (30,000 cps) and 5.00 parts of benzoyl chloride in to a reaction kettle. This mixture was stirred for one-half hour until the ingredients were homogeneously mixed. A polyol mixture which contained 1303 parts of Poly-G-36-232, 1983 parts of Pluracol P-100, 125 parts of Aerosil 974 and 170 parts of THANCAT DMDEE was then added to the reaction kettle. After the exotherm of the reaction subsided, the mixture was held at 50° C. for one hour without heating. One hundred parts by weight of the prepolymer were transferred to a 40 gallon Ross HDM-40 double planetary mixture under dry nitrogen. 5.33 parts by weight of Dow Corning 200 Silicone Fluid, 30,000 cps was added and mixed into the prepolymer. A vacuum was then applied to remove gases. The vacuum was broken with nitrogen and 3.98 parts by weight of Aerosil R-972, 2.18 parts by weight of Polyox N-10 and 1.09 parts by weight of mineral oil were added to the prepolymer. The vacuum was reapplied and the mixture was blended for 30 minutes at room temperature. The viscosity of the product was 600,000 cps (Brookfield viscometer Model RVF, 4 RPM, 23° C., #7 spindle). The product was packaged in a moisture impervious package. The formulation was applied to a cast and went on smoothly with minimum tackiness.

EXAMPLE 9

Cylinders of cast material were prepared by forming a test cylinder around a dowel which was approximately two and three-quarter inches in diameter. The test cylinders were multiple wraps of four inch wide casting tape. Test cylinders were made with four or five layers of a standard polyurethane-fiberglass casting tape. In some of the test cylinders, six grams of the polyurethane reinforcing resin of Example 8 were applied as a two inch wide strip around the circumference of the four inch cylinder. A five pound projectile was dropped from a height of two feet onto the top of the cylinders on the area where the reinforcing resin was applied and the integrity of the cylinders was determined by observing cracks and delamination of the various layers of the fiberglass material. Three or more cylinders were made for each test and the number of drops of the projectile to failure were noted and the averages reported. The results are reported in the table below. Cylinders A were made from four layers of fiberglass casting tape with no reinforcing resin. Cylinders B were made with four layers of fiberglass tape and six grams of the liquid reinforcing resin was applied between the second and third layer of the fiberglass tape as the tape was wrapped. Cylinders C were made from five layers of fiberglass casting tape with no reinforcing resin. Cylinders D were made with five layers of fiberglass casting tape, and six grams of the prepolymer reinforcing material was applied between the third and fourth layer of the casting tape. The results of the test are shown in the following Table.

In the following Table the data shows that in the samples where the polyurethane reinforcing resin was applied the cylinders could withstand more impact before breaking.

TABLE

| Sample | No. of impacts to Break Cylinder |
|--------|----------------------------------|
| A      | 3                                |
| B      | 11                               |
| C      | 20                               |
| D      | 42                               |

We claim:

1. A method of reinforcing a polyurethane cast comprising applying to the cast while the cast is wet with water a liquid composition comprising an aromatic polyisocyanate and a polyol in an equivalent ratio of from 2.1 to 15.1, a catalyst in an amount of from 0.1 to 10% based on the weight of the composition, an antifoam agent in an amount of from 0.7 to 7.5% based on the weight of the formulation a thickening agent in an amount of from 2 to 6% by weight of the formulation from 0.5% to 2% by weight mineral oil and a 0.5% to 3% by weight water soluble polymer selected from the group consisting of polyvinylpyrrolidone having a molecular weight of from 100,000 to 1,000,000 and a polymer having repeating units of the structure $(O-CH_2CH_2)_n$ where n is an integer such that the molecular weight of the water soluble polymer is from 50,000 to 4,000,000, said composition having a viscosity of between 100,000 and 1,000,000.

2. The method of claim 1 in which the composition is applied at a rate of from ½ to 1 gram per square inch of cast surface to be reinforced.

3. The method of claim 1 in which the composition has a viscosity is between 300,000 and 800,000.

4. The method of claim 1 in which the antifoam agent is polydimethylsiloxane.

5. The method of claim 1 in which the thickening agent is fumed silica.

6. The process of claim 1 in which the water soluble polymer is poly(ethylene oxide).

7. The process of claim 6 in the water soluble polymer has molecular weight between 100,000 and 3,000,000.

8. A moisture impervious container having a volume of from 2 to 16 ounces and a sealable opening at one end filled with a liquid composition comprising an aromatic polyisocyanate and a polyol in an equivalent ratio of from 2.1 to 15.1, a catalyst in an amount of from 0.1 to 10% based on the weight of the composition, an antifoam agent in an amount of from 0.7 to 7.5% based on the weight of the composition, a thickening agent in an amount of from 2 to 5% by weight of the composition, from 0.5% to 2% by weight mineral oil and a 0.5% to 3% by weight of a water soluble polymer selected from the group consisting of polyvinylpyrrolidone having a molecular weight of from 100,000 to 1,000,000 and a polymer having repeating units of the structure $(O-CH_2CH_2)_n$ where n is an integer such that the molecular weight of the water soluble polymer is from 50,000 to 4,000,000, said composition having a viscosity of between 100,000 and 1,000,000, and said composition capable of foaming in a ratio of from 4 to 1 to 16 to 1.

9. The container of claim 6 in which the viscosity of the composition is between 300,000 and 500,000.

10. The container of of claim 6 in which the antifoam agent is polydimethylsiloxane.

11. The container of claim 6 in which the thickening agent is fumed silica.

12. The process of claim 1 in which the water soluble polymer is poly(ethylene oxide).

13. The process of claim 6 in the water soluble polymer has molecular weight between 100,000 and 3,000,000.

* * * * *